(12) United States Patent
Saito et al.

(10) Patent No.: US 7,851,032 B2
(45) Date of Patent: Dec. 14, 2010

(54) LIQUID CRYSTAL COMPOSITION AND LIQUID CRYSTAL DISPLAY DEVICE

(75) Inventors: Masayuki Saito, Chiba (JP); Teru Shimada, Chiba (JP)

(73) Assignees: Chisso Corporation, Osaka (JP); Chisso Petrochemical Corporation, Tokyo (JP)

(*) Notice: Subject to any disclaimer, the term of this patent is extended or adjusted under 35 U.S.C. 154(b) by 36 days.

(21) Appl. No.: 12/437,212

(22) Filed: May 7, 2009

(65) Prior Publication Data

US 2009/0278089 A1    Nov. 12, 2009

(30) Foreign Application Priority Data

May 8, 2008    (JP) .............................. 2008-122422

(51) Int. Cl.
*C09K 19/30*    (2006.01)
*C09K 19/12*    (2006.01)
*C09K 19/20*    (2006.01)
*C07C 25/24*    (2006.01)
*C07C 43/215*    (2006.01)
*C07C 43/225*    (2006.01)

(52) U.S. Cl. .............. 428/1.1; 252/299.63; 252/299.66; 252/299.67; 568/642; 568/643; 570/128

(58) Field of Classification Search ................... 428/1.1; 252/299.63, 299.66, 299.67; 568/642, 643; 570/128
See application file for complete search history.

(56) References Cited

U.S. PATENT DOCUMENTS 6,468,608 B1 * 10/2002 Bremer et al. ............... 428/1.1
6,548,126 B1 *  4/2003 Sasada et al. ................ 428/1.1

FOREIGN PATENT DOCUMENTS

JP    2007002132    1/2007

* cited by examiner

*Primary Examiner*—Shean C Wu
(74) *Attorney, Agent, or Firm*—Hogan Lovells US LLP

(57) ABSTRACT

A liquid crystal composition is provided that satisfies at least one characteristic among the characteristics such as a high maximum temperature of a nematic phase, a low minimum temperature of a nematic phase, a small viscosity, a large optical anisotropy, a large dielectric anisotropy, a large specific resistance, a high stability to ultraviolet light and a high stability to heat, or is properly balanced regarding at least two characteristics. An AM device is provided that has a short response time, a large voltage holding ratio, a large contrast ratio, a long service life and so forth. The liquid crystal composition contains a specific compound having especially negatively large dielectric anisotropy as the first component, a specific bicyclic compound having a small viscosity as the second component, a specific compound having a high maximum temperature as the third component, a specific compound having a negatively large dielectric anisotropy, a low minimum temperature as the fourth component. The liquid crystal composition has a negative dielectric anisotropy. The liquid crystal display device contains the liquid crystal composition.

23 Claims, No Drawings

LIQUID CRYSTAL COMPOSITION AND LIQUID CRYSTAL DISPLAY DEVICE

CROSS REFERENCE TO RELATED APPLICATIONS

This application claims priority under 35 U.S.C. §119 to Japanese Patent Application No. JP 2008-122422, filed May 8, 2008, which application is expressly incorporated herein by reference in its entirety.

BACKGROUND OF THE INVENTION

1. Field of the Invention

The invention relates to a liquid crystal composition suitable for use in an active matrix (AM) device, and an AM device containing the composition. More specifically, the invention relates to a liquid crystal composition having a negative dielectric anisotropy, and also relates to a device of an in plane switching (IPS) mode, a vertical alignment (VA) mode or a polymer sustained alignment (PSA) mode containing the composition.

2. Related Art

In a liquid crystal display device, classification based on an operating mode of liquid crystals includes phase change (PC), twisted nematic (TN), super twisted nematic (STN), electrically controlled birefringence (ECB), optically compensated bend (OCB), in-plane switching (IPS), vertical alignment (VA), polymer sustained alignment (PSA) and so forth. Classification based on a driving mode of the device includes a passive matrix (PM) and an active matrix (AM). PM is further classified into static, multiplex and so forth, and AM is classified into a thin film transistor (TFT), a metal insulator metal (MIM) and so forth. TFT is further classified into amorphous silicon and polycrystal silicon. The latter is classified into a high temperature type and a low temperature type according to a production process. Classification based on a light source includes a reflection type utilizing a natural light, a transmission type utilizing a backlight and a semi-transmission type utilizing both the natural light and the backlight.

These devices contain a liquid crystal composition having suitable characteristics. The liquid crystal composition has a nematic phase. General characteristics of the composition should be improved to obtain an AM device having good general characteristics. Table 1 below summarizes a relationship between the general characteristics of the two. The general characteristics of the composition will be explained further based on a commercially available AM device. A temperature range of a nematic phase relates to the temperature range in which the device can be used. A desirable maximum temperature of the nematic phase is approximately 70° C. or more and a desirable minimum temperature is approximately −10° C. or less. The viscosity of the composition relates to the response time of the device. The rotation viscosity of the composition also relates to the response time of the device. A short response time is desirable for displaying a moving image. Accordingly, a small viscosity of the composition is desirable. A small viscosity at a low temperature is more desirable.

TABLE 1

General Characteristics of Liquid Crystal Composition and AM Device

| No | General Characteristics of a Composition | General Characteristics of an AM Device |
|---|---|---|
| 1 | Temperature range of a nematic phase is wide | Usable temperature range is wide |
| 2 | Viscosity is small[1) | Response time is short |
| 3 | Optical anisotropy is suitable | Contrast ratio is large |
| 4 | Dielectric anisotropy is positively or negatively large | Threshold voltage is low, electric power consumption is small, and contrast ratio is large |
| 5 | Specific resistance is large | Voltage holding ratio is large, and a contrast ratio is large |
| 6 | It is stable to ultraviolet light and heat | Service life is long |

[1)A liquid crystal composition can be injected into a cell in a short time.

The optical anisotropy of the composition relates to the contrast ratio of the device. A product ($\Delta n \times d$) of the optical anisotropy ($\Delta n$) of the composition and the cell gap (d) of the device is designed to maximize the contrast ratio. A suitable value of the product depends on the kind of operation mode. In a device having a VA mode, a suitable value is in a range of from approximately 0.30 μm to approximately 0.40 μm, and in a device having an IPS mode, a suitable value is in a range of from approximately 0.20 μm to approximately 0.30 μm. In this case, a composition having a large optical anisotropy is desirable for a device having a small cell gap. A large dielectric anisotropy of the composition contributes to a low threshold voltage, a small electric power consumption and a large contrast ratio of the device. Accordingly, a large dielectric anisotropy is desirable. A large specific resistance of the composition contributes to a large voltage holding ratio and a large contrast ratio of the device. Accordingly, a composition having a large specific resistance is desirable at room temperature and also at a high temperature in the initial stage. A composition having a large specific resistance is desirable at room temperature and also at a high temperature after it has been used for a long time. A stability of the composition to an ultraviolet light and heat relates to a service life of the liquid crystal display device. In the case where the stability is high, the device has a long service life. These characteristics are desirable for an AM device used in a liquid crystal projector, a liquid crystal television and so forth.

In an AM device having a TN mode, a composition having a positive dielectric anisotropy is used. In an AM device having a VA mode, a composition having a negative dielectric anisotropy is used. In an AM device having an IPS mode, a composition having a positive or negative dielectric anisotropy is used. In an AM device having a PSA mode, a composition having a positive or negative dielectric anisotropy is used. Examples of the liquid crystal composition having a negative dielectric anisotropy are disclosed in JP 2007-2132A.

A desirable AM device is characterized as having a usable temperature range that is wide, a response time that is short, a contrast ratio that is large, a threshold voltage that is low, a voltage holding ratio that is large, a service life that is long, and so forth. Even one millisecond shorter response time is desirable. Thus, the composition having characteristics such as a high maximum temperature of a nematic phase, a low minimum temperature of a nematic phase, a small viscosity, a large optical anisotropy, a large dielectric anisotropy, a large specific resistance, a high stability to an ultraviolet light, a high stability to heat, and so forth is especially desirable.

SUMMARY OF THE INVENTION

The invention concerns a liquid crystal composition having a negative dielectric anisotropy that includes two components, wherein the first component is at least one compound selected from the group of compounds represented by formula (1), the second component is at least one compound selected from the group of compounds represented by formula (2):

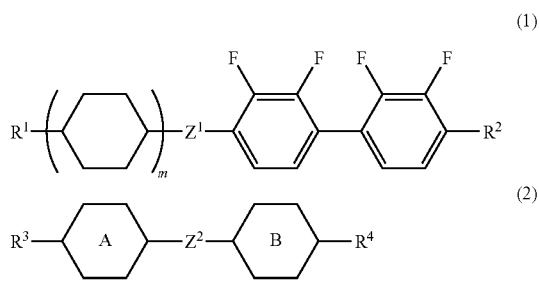

wherein $R^1$, $R^2$, $R^3$ and $R^4$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine; ring A and ring B are each independently 1,4-cyclohexylene or 1,4-phenylene; $Z^1$ is methyleneoxy or carbonyloxy; $Z^2$ is a single bond, ethylene, vinylene, methyleneoxy or carbonyloxy; and m is 1 or 2.

The invention also concerns a liquid crystal display device that includes the liquid crystal composition, and so forth.

DETAILED DESCRIPTION OF THE INVENTION

The terms used in the specification and claims are defined as follows. The liquid crystal composition and/or the liquid crystal display device of the invention may occasionally be expressed simply as "the composition" or "the device," respectively. A liquid crystal display device is a generic term for a liquid crystal display panel and a liquid crystal display module. The "liquid crystal compound" is a generic term for a compound having a liquid crystal phase such as a nematic phase, a smectic phase and so forth, and also for a compound having no liquid crystal phase but being useful as a component of a composition. The useful compound contains, for example, a 6-membered ring such as 1,4-cyclohexylene and 1,4-phenylene, and a rod like molecular structure. An optically active compound or a polymerizable compound may occasionally be added to the composition. Even in the case where the compound is a liquid crystal compound, the compound is classified into an additive. At least one compound selected from a group of compounds represented by formula (1) may be abbreviated to "the compound (1)." The "compound (1)" means one compound or two or more compounds represented by formula (1). The other formulas are applied with the same rules. The term "arbitrary" means that not only the position but also the number are arbitrary, but the case where the number is zero is not included.

A higher limit of a temperature range of a nematic phase may be abbreviated to "a maximum temperature." A lower limit of a temperature range of a nematic phase may be abbreviated to "a minimum temperature." "A specific resistance is large" means that the composition has a large specific resistance at room temperature and also nearly at the maximum temperature of a nematic phase in the initial stage, the composition has a large specific resistance at room temperature and also nearly at the maximum temperature of a nematic phase even after it has been used for a long time. "A voltage holding ratio is large" means that a device has a large voltage holding ratio at room temperature and also nearly at the maximum temperature of a nematic phase in the initial stage, the device has a large voltage holding ratio at room temperature and also nearly at the maximum temperature of a nematic phase even after it has been used for a long time. In the description of the characteristics such as optical anisotropy, the characteristics of the composition such as the optical anisotropy and so forth are values measured in the methods disclosed in Examples. The first component includes one compound or two or more compounds. "A ratio of the first component" means the percentage by weight (% by weight) of the first component based on the total weight of liquid crystal composition. A ratio of the second component and so forth are applied with the same rule. A ratio of an additive mixed with the composition means the percentage by weight (% by weight) based on the total weight of liquid crystal composition.

In the chemical formulas of the component compounds, symbol $R^2$ is used in plural compounds. In these compounds, any two $R^2$ may be the same as or different from each other. In one case, for example, $R^2$ of the compound (1) is ethyl and $R^2$ of the compound (1-1) is ethyl. In another case, $R^2$ of the compound (1) is ethyl and $R^2$ of the compound (1-1) is propyl. This rule is also applicable to the symbols $R^3$, $R^4$ and so forth. CL in the chemical formulas is chlorine.

One of the advantages of the invention is to provide a liquid crystal composition that satisfies at least one characteristic among the characteristics such as a high maximum temperature of a nematic phase, a low minimum temperature of a nematic phase, a small viscosity, a large optical anisotropy, a large dielectric anisotropy, a large specific resistance, a high stability to ultraviolet light and a high stability to heat and so forth. Another advantage of the invention is to provide a liquid crystal composition that is properly balanced regarding at least two characteristics among many characteristics. Another advantage of the invention is to provide a liquid crystal display device that contains the liquid crystal composition. Another of the advantage of the invention is to provide a liquid crystal composition that has a large optical anisotropy, a large dielectric anisotropy, a high stability to ultraviolet light and so forth, and is to provide an AM device that has a short response time, a large voltage holding ratio, a large contrast ratio, a long service life and so forth.

The invention has the following features.

1. The invention concerns a liquid crystal composition having a negative dielectric anisotropy that includes two components, wherein the first component is at least one compound selected from the group of compounds represented by formula (1), the second component is at least one compound selected from the group of compounds represented by formula (2):

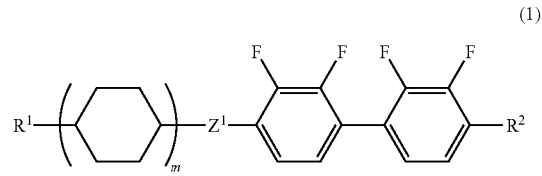

-continued

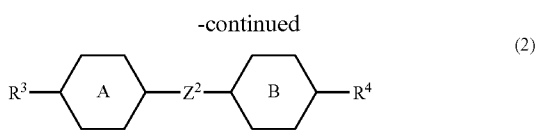
(2)

wherein $R^1$, $R^2$, $R^3$ and $R^4$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine; ring A and ring B are each independently 1,4-cyclohexylene or 1,4-phenylene; $Z^1$ is methyleneoxy or carbonyloxy; $Z^2$ is a single bond, ethylene, vinylene, methyleneoxy or carbonyloxy; and m is 1 or 2.

2. The liquid crystal composition according to item 1, wherein the first component is at least one compound selected from the group of compounds represented by formula (1-1):

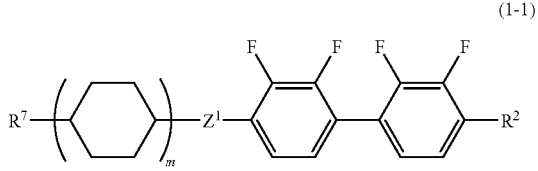
(1-1)

wherein $R^7$ is alkenyl having 2 to 12 carbons; $R^2$ is alkyl having 1 to 12 carbons, alkoxy having 1 to 12 carbons or alkenyl having 2 to 12 carbons or alkenyl having 2 to 12 carbons in which arbitrary hydrogen is replaced by fluorine; $Z^1$ is methyleneoxy or carbonyoxy; and m is 1 or 2.

3. The liquid crystal composition according to item 1 or 2, wherein the second component is at least one compound selected from the group of compounds represented by formula (2-1) to (2-3):

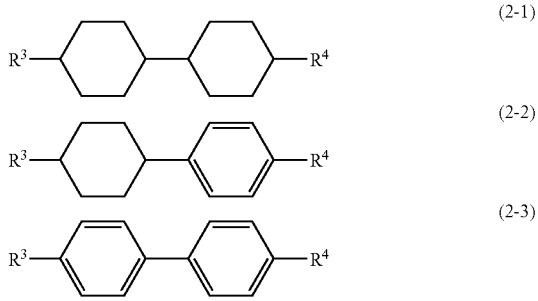
(2-1)

(2-2)

(2-3)

wherein $R^3$ and $R^4$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine.

4. The liquid crystal composition according to item 3, wherein the second component is at least one compound selected from the group of compounds represented by formula (2-1).

5. The liquid crystal composition according to item 3, wherein the second component is a mixture of at least one compound selected from the group of compounds represented by formula (2-1) and at least one compound selected from the group of compounds represented by formula (2-3).

6. The liquid crystal composition according to any one of items 1 to 5, a ratio of the first component is from approximately 5% by weight to approximately 40% by weight, a ratio of the second component is from approximately 25% by weight to approximately 70% by weight.

7. The liquid crystal composition according to any one of items 1 to 6, wherein the composition further comprises at least one compound selected from the group of compounds represented by formulas (3) as a third component:

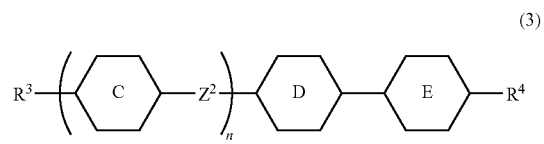
(3)

wherein $R^3$ and $R^4$ are each independently alkyl having 1 to 12 carbons, alkoxy having 1 to 12 carbons or alkenyl having 2 to 12 carbons, alkenyl having 2 to 12 carbons in which arbitrary hydrogen is replaced by fluorine; ring C, ring D and ring E are each independently 1,4-cyclohexylene, 1,4-phenylene, 2-fluoro-1,4-phenylene or 2,5-difluoro-1,4-phenylene; $Z^2$ is independently a single bond, ethylene, vinylene, methyleneoxy or carbonyloxy; and n is 1 or 2.

8. The liquid crystal composition according to item 7, wherein the third component is at least one compound selected from the group of compounds represented by formula (3-1) to (3-7):

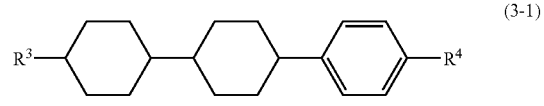
(3-1)

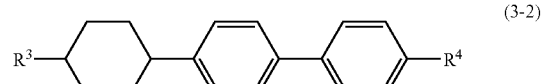
(3-2)

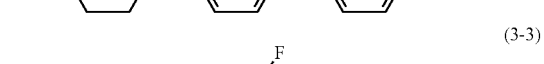
(3-3)

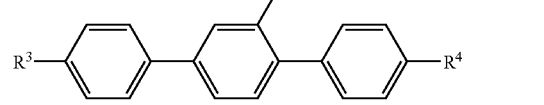
(3-4)

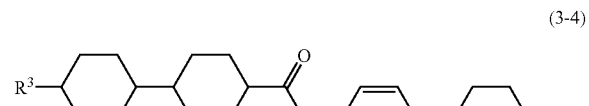
(3-5)

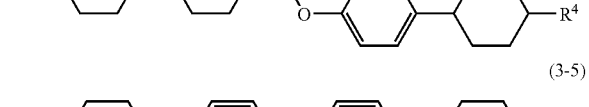
(3-6)

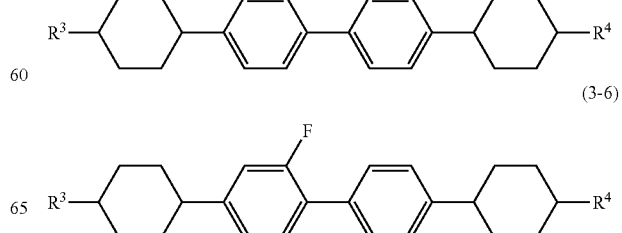

-continued (3-7)

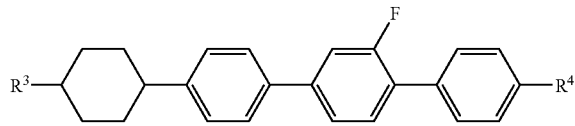

wherein $R^3$ and $R^4$ are each independently alkyl having 1 to 12 carbons, alkoxy having 1 to 12 carbons or alkenyl having 2 to 12 carbons, alkenyl having 2 to 12 carbons in which arbitrary hydrogen is replaced by fluorine.

9. The liquid crystal composition according to item 8, wherein the third component is at least one compound selected from the group of compounds represented by formula (3-1).

10. The liquid crystal composition according to item 8, wherein the third component is at least one compound selected from the group of compounds represented by formula (3-3).

11. The liquid crystal composition according to item 8, wherein the third component is a mixture of at least one compound selected from the group of compounds represented by formula (3-1) and at least one compound selected from the group of compounds represented by formula (3-3).

12. The liquid crystal composition according to any one of items 7 to 11, wherein a ratio of the third component is from approximately 5% by weight to approximately 30% by weight based on the total weight of the liquid crystal composition.

13. The liquid crystal composition according to any one of items 1 to 12, wherein the composition further comprises at least one compound selected from the group of compounds represented by formula (4) as a fourth component:

(4)

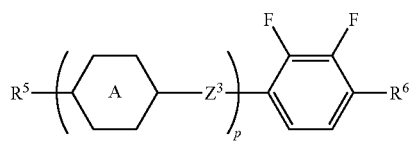

wherein $R^5$ and $R^6$ are each independently alkyl having 1 to 12 carbons, alkoxy having 1 to 12 carbons or alkenyl having 2 to 12 carbons, alkenyl having 2 to 12 carbons in which arbitrary hydrogen is replaced by fluorine; ring A is independently 1,4-cyclohexylene or 1,4-phenylene; $Z^3$ is independently a single bond, ethylene, methyleneoxy or carbonyloxy; and p is 1, 2 or 3.

14. The liquid crystal composition according to item 13, wherein the fourth component is at least one compound selected from the group of compounds represented by formulas (4-1) to (4-6):

(4-1)

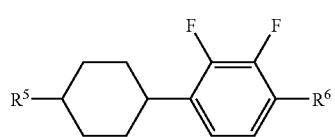

(4-2)

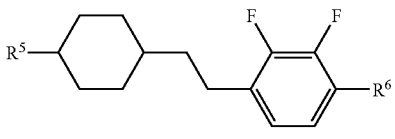

(4-3)

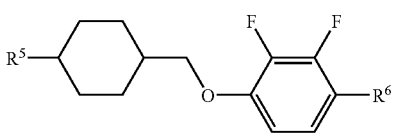

(4-4)

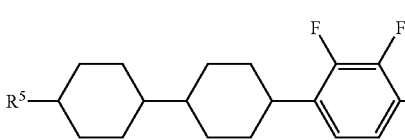

(4-5)

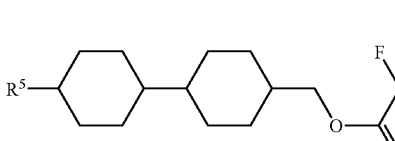

(4-6)

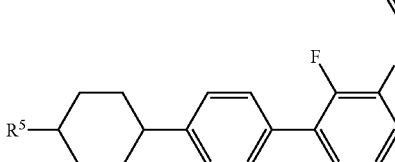

wherein $R^5$ and $R^6$ are each independently alkyl having 1 to 12 carbons, alkoxy having 1 to 12 carbons, alkenyl having 2 to 12 carbons, or alkenyl having 2 to 12 carbons in which arbitrary hydrogen is replaced by fluorine.

15. The liquid crystal composition according to item 14, wherein the fourth component is at least one compound selected from the group of compounds represented by formula (4-1).

16. The liquid crystal composition according to item 14, wherein the fourth component is a mixture of at least one compound selected from the group of compounds represented by formula (4-1) and at least one compound selected from the group of compounds represented by formula (4-4).

17. The liquid crystal composition according to item 14, wherein the fourth component is a mixture of at least one compound selected from the group of compounds represented by formula (4-1) and at least one compound selected from the group of compounds represented by formula (4-6).

18. The liquid crystal composition according to item 14, wherein the fourth component is a mixture of at least one compound selected from the group of compounds represented by formula (4-1), at least one compound selected from the group of compounds represented by formula (4-4) and at least one compound selected from the group of compounds represented by formula (4-6).

19. The liquid crystal composition according to any one of items 13 to 18, wherein a ratio of the fourth component is from approximately 5% by weight to approximately to 60% by weight based on the total weight of the liquid crystal composition.

20. The liquid crystal composition according to any one of items 1 to 19, wherein the composition has a maximum temperature of a nematic phase of approximately 70° C. or more, an optical anisotropy (25° C.) at a wavelength of 589 nm of approximately 0.08 or more, and a dielectric anisotropy (25° C.) at a frequency of 1 kHz of approximately −2 or less.

21. A liquid crystal device display that includes the liquid crystal composition according to any one of items 1 to 20.

22. The liquid crystal composition according to item 21, wherein the liquid crystal display device has an operation mode of a VA mode, an IPS mode or a PSA mode, and has a driving mode of an active matrix mode.

23. The compounds represented by formula (1-1):

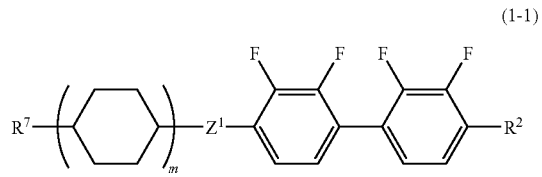

(1-1)

wherein $R^7$ is alkenyl having 2 to 12 carbons; $R^2$ is alkyl having 1 to 12 carbons, alkoxy having 1 to 12 carbons, alkenyl having 2 to 12 carbons or alkenyl having 2 to 12 carbons in which arbitrary hydrogen is replaced by fluorine; $Z^1$ is methyleneoxy or carbonyloy; and m is 1 or 2.

The invention further includes: (1) the composition described above, wherein the composition further contains an optically active compound; (2) the composition described above, wherein the composition further contains an additive, such as an antioxidant, an ultraviolet light absorbent, an antifoaming agent, a polymerizable compound, a polymerization initiator and so forth; (3) an AM device containing the composition described above; (4) a device having a TN, ECB, OCB, IPS, VA or PSA mode, containing the composition described above; (5) a device of a transmission type, containing the composition described above; (6) use of the composition described above as a composition having a nematic phase; and (7) use as an optically active composition by adding an optically active compound to the composition described above.

The composition of the invention will be explained in the following order. First, the constitution of component compounds in the composition will be explained. Second, the main characteristics of the component compounds and the main effects of the compounds on the composition will be explained. Third, combinations of components in the composition, desirable ratios of the component compounds and the basis thereof will be explained. Fourth, a desirable embodiment of the component compounds will be explained. Fifth, examples of the component compound will be shown. Sixth, additives that may be added to the composition will be explained. Seventh, the preparation methods of the component compound will be explained. Lastly, use of the composition will be explained.

First, the constitution of component compounds in the composition will be explained. The composition of the invention is classified into the composition A and the composition B. The composition A may further contain other compounds such as another liquid crystal compound, an additive, an impurity, and so forth. "Another liquid crystal compound" is different from the compound (1), the compound (2), the compound (3), and the compound (4). Such a liquid crystal compound is mixed with the composition for the purpose of adjusting the characteristics of the composition. Among the other liquid crystal compounds, an amount of a cyano compound is desirably small from the viewpoint of stability to heat or ultraviolet light. The more desirable amount of a cyano compound is 0% by weight. The additive includes an optically active compound, an antioxidant, an ultraviolet light absorbent, a coloring matter, an antifoaming agent, a polymerizable compound, a polymerization initiator and so forth. The impurity is a compound and so forth contaminated in the process such as the synthesis of a component compound and so forth. Even when the compound is a liquid crystal compound, it is classified into an impurity herein.

The composition B essentially consists of the compounds selected from the compound (1), the compound (2), the compound (3), and the compound (4). The term "essentially" means that the composition does not contain a liquid crystal compound that is different from these compounds, except for the additive and the impurity. The components of the composition B are fewer than those of the composition A. The composition B is preferable to the composition A from the viewpoint of cost reduction. The composition A is preferable to the composition B, because characteristics of the composition A can be further adjusted by mixing other liquid crystal compounds.

Second, the main characteristics of the component compounds and the main effects of the compounds on the composition will be explained. The main characteristics of the component compounds are summarized in Table 2. In Table 2, the symbol L represents large or high, the symbol M represents a middle degree, and the symbol S represents small or low. The symbols L, M and S are classification based on qualitative comparison among the component compounds.

TABLE 2

| | Characteristics of Compounds | | | |
|---|---|---|---|---|
| | Compound | | | |
| | (1) | (2) | (3) | (4) |
| Maximum temperature | M-L | S | M-L | S-M |
| Viscosity | L | S | M | M |
| Optical anisotropy | M | S-M | M-L | M-L |
| Dielectric anisotropy | L[1] | 0 | 0 | M[1] |
| Specific resistance | L | L | L | L |

[1]The value of dielectric anisotropy is negative, and the symbol indicates the absolute value.

The main effects of the component compounds to the characteristics of the composition upon mixing the component compounds in the composition are as follows. The compound (1) increases the maximum temperature and the absolute value of the dielectric anisotropy. The compound (2) decreases the viscosity. The compound (3) increases the maximum temperature. The compound (4) increases the absolute value of the dielectric anisotropy and decreases the minimum temperature.

Third, combinations of components in the composition, desirable ratios of the component compounds and the basis thereof will be explained. Examples of the combinations of the components in the composition include (first component+ second component), (first component+second component+ third component), (first component+second component+ fourth component) and (first component+second component+third component+fourth component).

A desirable ratio of the first component is approximately 5% by weight or more for increasing the absolute value of the dielectric anisotropy, and is approximately 40% by weight or less for decreasing the minimum temperature. A more desirable ratio is from approximately 5% by weight to approximately 35% by weight. A particularly desirable ratio is from approximately 5% by weight to approximately 30% by weight.

A desirable ratio of the second component is approximately 25% by weight or more for decreasing the viscosity, and is approximately 70% by weight or less for increasing absolute value of the dielectric anisotropy. A more desirable ratio is from approximately 30% by weight to approximately 65% by weight. A particularly desirable ratio is from approximately 35% by weight to approximately 60% by weight.

A desirable ratio of the third component is approximately 5% by weight or more for increasing the maximum temperature, and is approximately 30% by weight or less for increasing the absolute value of the dielectric anisotropy. A more desirable ratio is from approximately 5% by weight to approximately 25% by weight. A particularly desirable ratio is from approximately 5% by weight to approximately 20% by weight.

A desirable ratio of the fourth component is approximately 5% by weight or more for increasing the absolute value of dielectric anisotropy, and is approximately 60% by weight or less for decreasing the viscosity. A more desirable ratio is from approximately 10% by weight to approximately 55% by weight. A particularly desirable ratio is from approximately 15% by weight to approximately 50% by weight.

Fourth, a desirable embodiment of the component compound will be explained. $R^1$, $R^2$, $R^3$, $R^4$, $R^5$ and $R^6$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine. Desirable $R^1$ and $R^5$ are each independently alkenyl having 2 to 12 carbons for decreasing the minimum temperature. Desirable $R^2$ and $R^6$ are each independently alkoxy having 1 to 12 carbons for increasing the absolute value of the dielectric anisotropy. Desirable $R^3$ and $R^4$ are each independently alkyl having 1 to 12 carbons for increasing the stability to ultraviolet light or heat, or alkenyl having 2 to 12 carbons for decreasing the minimum temperature. $R^7$ is alkenyl having 2 to 12 carbons.

Desirable alkyl is methyl, ethyl, propyl, butyl, pentyl, hexyl, heptyl, or octyl. More desirable alkyl is ethyl, propyl, butyl, pentyl or heptyl for decreasing a viscosity.

Desirable alkoxy is methoxy, ethoxy, propoxy, butoxy, pentyloxy, hexyloxy, or heptyloxy. More desirable alkoxy is methoxy or ethoxy for decreasing a viscosity.

Desirable alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. More desirable alkenyl is vinyl, 1-propenyl, 3-butenyl, or 3-pentenyl for decreasing a viscosity. A desirable configuration of —CH═CH— in these alkenyls depends on the position of a double bond. Trans is desirable in the alkenyl such as 1-propenyl, 1-butenyl, 1-pentenyl, 1-hexenyl, 3-pentenyl, and 3-hexenyl for decreasing the viscosity. Cis is desirable in the alkenyl such as 2-butenyl, 2-pentenyl and 2-hexenyl. In these alkenyls, linear alkenyl is preferable to branched alkenyl.

Preferred examples of alkenyl in which arbitrary hydrogen is replaced by fluorine include 2,2-difluorovinyl, 3,3-difluoro-2-propenyl, 4,4-difluoro-3-butenyl, 5,5-difluoro-4-pentenyl and 6,6-difluoro-5-hexenyl. More preferred examples thereof include 2,2-difluorovinyl and 4,4-difluoro-3-butenyl for decreasing the viscosity.

Ring A and ring B are each independently 1,4-cyclohexylene, or 1,4-phenylene, and when p is 2 or 3, two arbitrary rings A may be the same as or different from each other. Desirable ring A is 1,4-cyclohexylene for decreasing the viscosity. Ring C, ring D and ring E are each independently 1,4-cyclohexylene, or 1,4-phenylene, 2-fluoro-1,4-phenylene or 2,5-difluoro-1,4-phenylene and when n is 2, two rings C may be the same as or different from each other. When the rings are 2-fluoro-1,4-phenylene, 2,5-difluoro-1,4-phenylene, the directions of the rings are not limited. Desirable ring C, ring D and ring E are each independently 1,4-cyclohexylene for decreasing the viscosity or 1,4-phenylene for increasing the optical anisotropy.

$Z^1$ is methyleneoxy or carbonyloxy. Desirable $Z^1$ is carbonyloxy for increasing the maximum temperature. $Z^2$ is independently a single bond, ethylene, vinylene, methyleneoxy or carbonyloxy, and when n is 2, two $Z^2$ may be the same as or different from each other. Desirable $Z^2$ is a single bond for decreasing the viscosity. $Z^3$ is independently a single bond, ethylene, methyleneoxy or carbonyloxy, when p is 2 or 3, two arbitrary $Z^3$ may be the same as or different from each other. Desirable $Z^3$ is a single bond for decreasing the viscosity.

m is 1 or 2. Desirable m is 2 for increasing the maximum temperature.

n is 1 or 2. Desirable n is 1 for decreasing the viscosity.

p is 1,2 or 3. Desirable p is 1 for decreasing the minimum temperature.

Fifth, examples of the component compounds will be shown. In the desirable compounds described below, $R^8$ is independently linear alkyl having 1 to 12 carbons or linear alkoxy having 1 to 12 carbons. $R^9$ and $R^{10}$ are each independently linear alkyl having 1 to 12 carbons or linear alkenyl having 2 to 12 carbons. $R^{11}$ is independently linear alkenyl having 1 to 12 carbons. In these desirable compounds, trans is preferable to cis for the configuration of 1,4-cyclohexylene for increasing the maximum temperature.

Desirable compounds (1) are the compounds (1-1-1) to (1-1-4). More desirable compounds (1) are the compounds (1-1-1) and (1-1-2). Particularly desirable compounds (1) are (1-1-1). Desirable compounds (2) are the compounds (2-1-1) to compounds (2-3-1). More desirable compounds (2) are the compounds (2-1-1) and compounds (2-3-1). Particularly desirable compounds (2) are compounds (2-1-1). Desirable compounds (3) are the compounds (3-1-1) to compounds (3-7-1) and compounds (3-8). More desirable compounds (3) are the compounds (3-1-1), compounds (3-2-1), compounds (3-3-1), and compounds (3-7-1). Particularly desirable compounds (3) are compounds (3-1-1) and (3-3-1). Desirable compounds (4) are the compounds (4-1-1) to (4-6-1), and compounds (4-7) to compounds (4-8). More desirable compounds (4) are the compounds (4-1-1), (4-3-1), (4-4-1), (4-5-1) and (4-6-1). Particularly desirable compounds (4) are the compounds (4-1-1), (4-4-1) and (4-6-1).

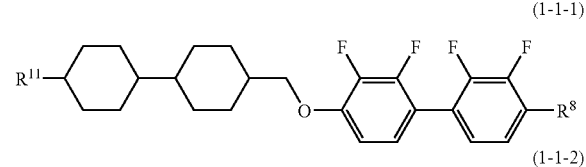

(1-1-1)

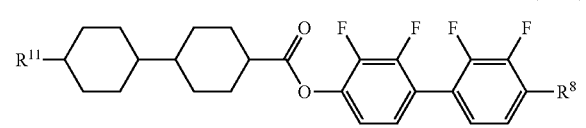

(1-1-2)

-continued (1-1-3)
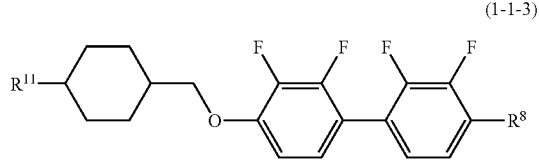

(1-1-4)
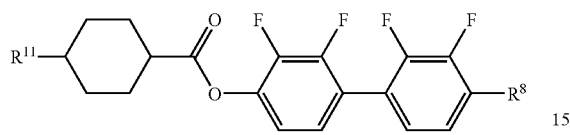

(2-1-1)
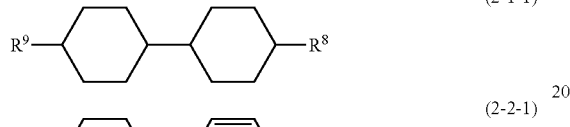

(2-2-1)
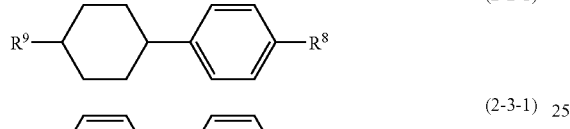

(2-3-1)
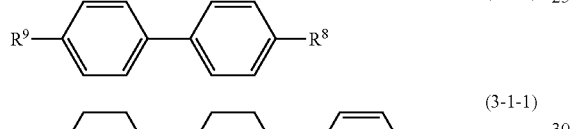

(3-1-1)

(3-2-1)
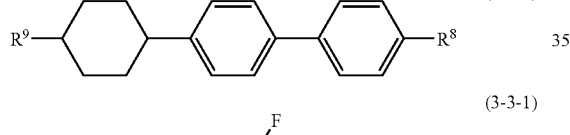

(3-3-1)
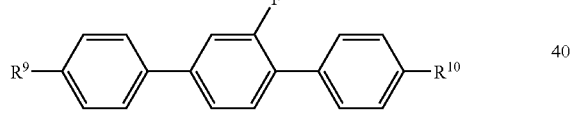

(3-4-1)
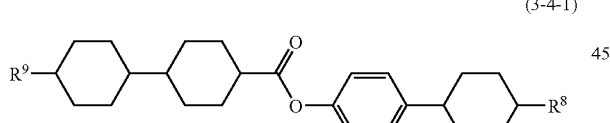

(3-5-1)
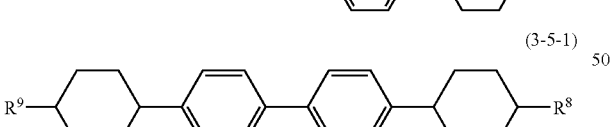

(3-6-1)
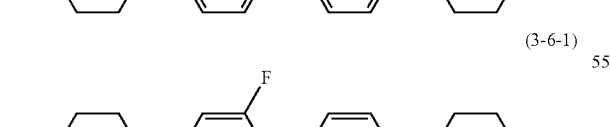

(3-7-1)
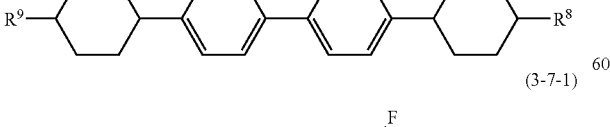

-continued (3-8)
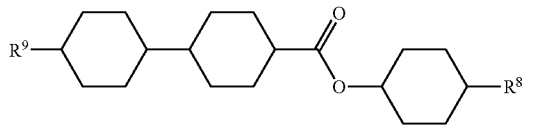

(4-1-1)
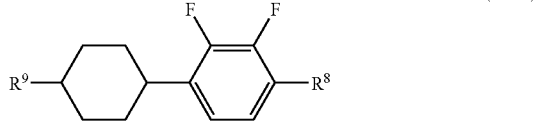

(4-2-1)
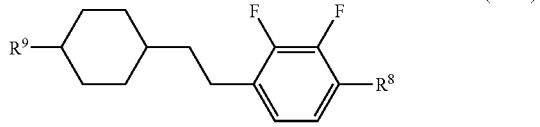

(4-3-1)
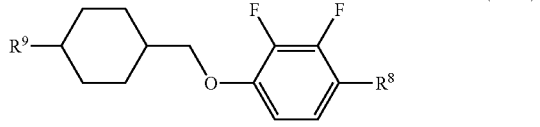

(4-4-1)
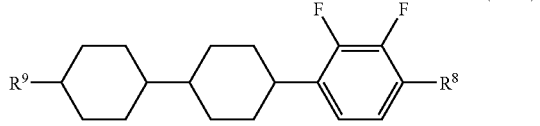

(4-5-1)
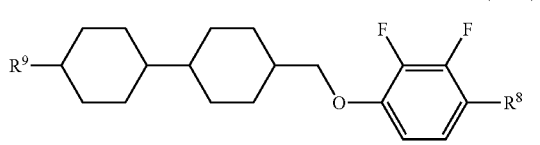

(4-6-1)
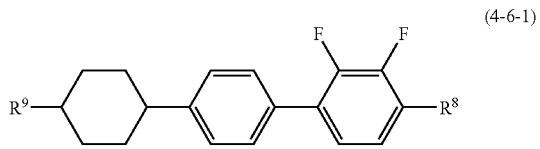

(4-7)
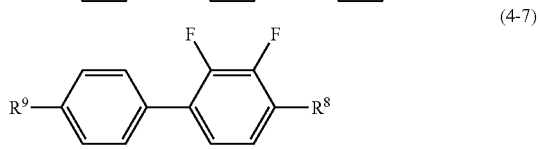

(4-8)
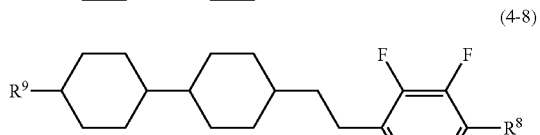

Sixth, additives capable of being mixed with the composition will be explained. The additives include an optically active compound, an antioxidant, an ultraviolet light absorbent, a coloring matter, an antifoaming agent, a polymerizable compound, a polymerization initiator and so forth. An optically active compound is mixed in the composition for inducing a helical structure of liquid crystal to provide a twist angle. Examples of the optically active compound include the compounds (5-1) to (5-4) below. A desirable ratio of the optically active compound is approximately 5% by weight or less, and a more desirable ratio thereof ranges from approximately 0.01% by weight to approximately 2% by weight.

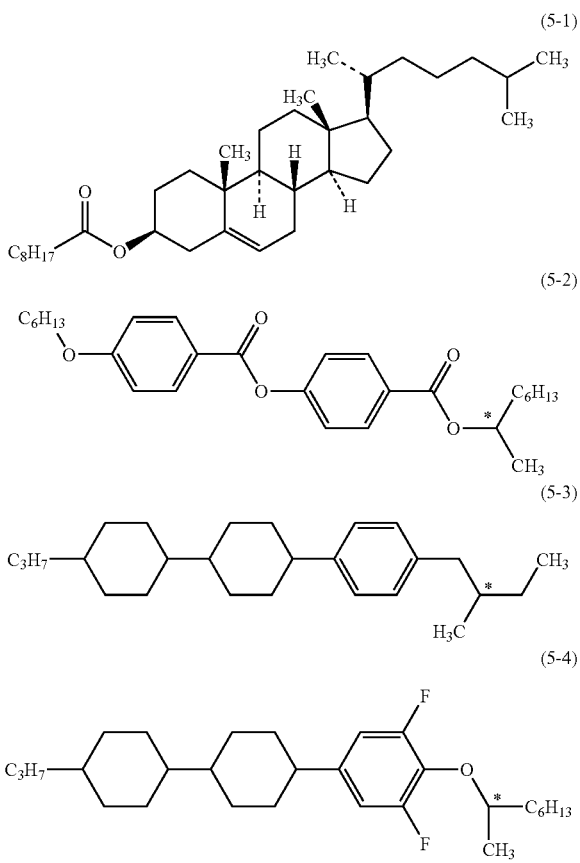

An antioxidant is mixed with the composition in order to avoid a decrease in specific resistance caused by heating in the air or to maintain a large voltage holding ratio at room temperature and also nearly at the maximum temperature even after the device has been used for a long time.

Preferred examples of the antioxidant include the compound (6):

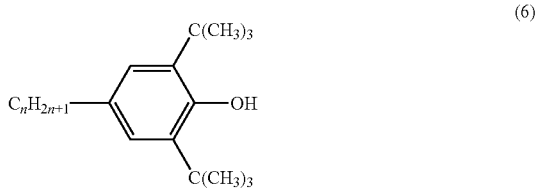

wherein n is an integer from 1 to 9. In the compound (6), desirable n are 1, 3, 5, 7, or 9. More desirable n are 1 or 7. When n is 1, the compound (6) has a large volatility, and is effective in preventing the decrease of specific resistance caused by heating in the air. When n is 7, the compound (6) has a small volatility, and is effective in maintaining a large voltage holding ratio at room temperature and also nearly at the maximum temperature even after the device has been used for a long time. A desirable ratio of the antioxidant is approximately 50 ppm or more in order to obtain the advantages thereof and is approximately 600 ppm or less in order to prevent the maximum temperature from being decreased and to prevent the minimum temperature from being increased. A more desirable ratio is from approximately 100 ppm to approximately 300 ppm.

Preferred examples of the ultraviolet light absorbent include a benzophenone derivative, a benzoate derivative and a triazole derivative. A light stabilizer having steric hindrance such as an amine is also desirable. A desirable ratio of the absorbent and the stabilizer is approximately 50 ppm or more for obtaining the advantages thereof and is approximately 10,000 ppm or less for preventing the maximum temperature from being decreased and preventing the minimum temperature from being increased. A more desirable ratio thereof ranges from approximately 100 ppm to approximately 10,000 ppm.

A dichroic dye such as an azo dye or an anthraquinone dye is mixed with the composition to suit for a device of a guest host (GH) mode. A desirable ratio of the dye ranges from approximately 0.01% by weight to approximately 10% by weight. An antifoaming agent such as dimethyl silicone oil or methylphenyl silicone oil is mixed with the composition for preventing foaming from occurring. A desirable ratio of the antifoaming agent is approximately 1 ppm or more for obtaining the advantages thereof and is approximately 1,000 ppm or less for preventing display failure from occurring. A more desirable ratio thereof ranges from approximately 1 ppm to approximately 500 ppm.

A polymerizable compound is mixed with the composition for applying the composition to a device having a PSA (polymer sustained alignment) mode. Preferred examples of the polymerizable compound include compounds having a polymerizable group, such as acrylate, methacrylate, vinyl, vinyloxy, propenyl ether, vinylketone, epoxy such as oxirane, oxetane, and so forth. Particularly preferred examples thereof include derivatives of acrylate or methacrylate. A desirable ratio of the polymerizable group is from approximately 0.05% by weight or more for obtaining the advantages thereof, and is approximately 10% by weight or less for preventing display failure from occurring. A more desirable ratio is from approximately 0.1% by weight to approximately 2% by weight. The polymerizable compound is polymerized preferably in the presence of a suitable initiator, such as a photopolymerization initiator and so forth, under radiation of ultraviolet light. Suitable conditions for polymerization and a suitable type and a suitable amount of the initiator have been known by a skilled person in the art and are disclosed in literatures. Examples of the photopolymerization initiator suitable for radical polymerization include Irgacure 651 (trade name), Irgacure 184 (trade name) and Darocure 1173 (trade name), all produced by Ciba Japan K.K. The polymerizable compound preferably contains a photopolymerization initiator in an amount of from approximately 0.1% by weight to approximately 5% by weight, and particularly preferably contains a photopolymerization initiator in an amount of from approximately 1% by weight to approximately 3% by weight.

Seventh, the preparation methods of the component compounds will be explained. These compounds can be prepared by known methods. The preparation method will be exemplified below. The compound (2-1-1) and compound (3-1-1) are synthesized by the method disclosed in JP H4-30382 A/1992. The compounds (4-1-1) and (4-4-1) are synthesized by the method disclosed in JP H2-503441 A/1990. The antioxidant is commercially available. The compound (6), wherein n is 1, is available, for example, from Sigma-Aldrich, Inc. The compound (6), wherein n is 7, and so forth are prepared by the method disclosed in U.S. Pat. No. 3,660,505.

The compounds for which preparation methods were not described above can be prepared according to the methods described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Kouza) (Maruzen, Inc.), and so forth. The composition is prepared according to known methods using the compounds thus obtained. For example, the component compounds are mixed and dissolved in each other by heating.

Last, use of the composition will be explained. The compositions of the invention mainly have a minimum temperature of approximately −10° C. or less, a maximum temperature of approximately 70° C. or more, and an optical anisotropy of approximately 0.07 to approximately 0.20. The device containing the composition has a large voltage holding ratio. The composition is suitable for an AM device. The composition is suitable especially for an AM device of a transmission type. The composition having an optical anisotropy of approximately 0.08 to approximately 0.25 and further having an optical anisotropy of approximately 0.10 to approximately 0.30 may be prepared by controlling ratios of the component compounds or by mixing other liquid crystal compounds. The composition can be used as a composition having a nematic phase and as an optically active composition by adding an optically active compound.

The composition can be used for an AM device. It can be also used for a PM device. The composition can be also used for an AM device and a PM device having a mode such as PC, TN, STN, ECB, OCB, IPS, VA, PSA and so forth. It is desirable to use the composition for an AM device having a TN, OCB or IPS mode. These devices may be of a reflection type, a transmission type or a semi-transmission type. It is desirable to use the composition for a device of a transmission type. It can be used for an amorphous silicon-TFT device or a polycrystal silicon-TFT device. The composition is also usable for a nematic curvilinear aligned phase (NCAP) device prepared by microcapsulating the composition, and for a polymer dispersed (PD) device in which a three dimensional net-work polymer is formed in the composition.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

EXAMPLES

The invention will be described in more detail with reference to examples below, but the invention is not construed as being limited to the examples.

All occurrences of "%" are by weight unless otherwise indicated. The resulting compounds were identified by magnetic nuclear resonance spectra obtained by $^1$H-NMR analysis, gas chromatograms obtained by gas chromatography (GC) analysis, and so forth. Accordingly, the analysis methods will be described below.

$^1$H-NMR Analysis:

DRX-500 (produced by Bruker Biospin Co., Ltd.) was used for measurement. A sample produced in the examples and so forth was dissolved in a deuterated solvent capable of dissolving the sample, such as $CDCl_3$, and the measurement was carried out at room temperature and 500 MHz with an accumulated number of 32. In the description of the resulting nuclear resonance spectra, s means a singlet, d means a doublet, t means a triplet, q means a quartet, and m means a multiplet, br means broard. Tetramethylsilane (TMS) was used as a standard substance indicating zero point of chemical shift δ.

GC Analysis:

Gas Chromatograph Model GC-14B made by Shimadzu was used for measurement. Capillary column CBP1-M25-025 (length: 25 m, bore: 0.22 mm, film thickness: 0.25 μm, dimethylpolysiloxane as stationary phase, no polarity) produced by Shimadzu Corp. was used as a column. Helium was used as a carrier gas and adjusted to a flow rate of 1 ml/min. The temperature of a sample vaporizing chamber was 280° C., and the temperature of the detector (FID) was 300° C.

The sample was dissolved in toluene to prepare a 1% by weight solution, and 1 μL of the resulting solution was injected into the sample vaporizing chamber. Chromatopac Model C-R6A, produced by Shimadzu Corp., or an equivalent thereof was used as a recorder. The gas chromatogram obtained showed a retention time of a peak and a peak area corresponding to the component compound.

Solvents for diluting the sample may also be chloroform, hexane, and so forth. The following capillary columns may also be used: a capillary column DB-1, produced by Agilent Technologies Inc. (length: 30 m, bore: 0.32 mm, film thickness: 0.25 μm), a capillary column HP-1, produced by Agilent Technologies Inc. (length: 30 m, bore: 0.32 mm, film thickness: 0.25 μm), a capillary column Rtx-1, produced by Restek Corporation (length: 30 m, bore: 0.32 mm, film thickness: 0.25 μm), and a capillary column BP-1, produced by SGE International Pty. Ltd. (length: 30 m, bore: 0.32 mm, film thickness: 0.25 μm).

An area ratio of each peak in the gas chromatogram corresponds to a ratio of the component compound. In general, the percentages by weight of the component compounds of the analyzed sample are not completely identical to the percentages by area of the peaks of the analyzed sample. According to the invention, however, the percentages by weight of the component compounds of the analyzed sample substantially correspond to the percentages by area of the peaks of the analyzed sample because the correction coefficient is substantially 1 when the aforementioned columns are used in the invention. The reason thereof is that there is no great difference between correction coefficient in liquid crystal compounds. In order to obtain accurately compositional ratios of liquid crystal compounds in a liquid crystal composition, an internal reference method in gas chromatogram is used. The liquid crystal compound (sample to be measured) and a liquid crystal compound as a reference (reference substance), which have been weighed accurately to prescribed amounts, are simultaneously measured by gas chromatography, and a relative intensity of an area ratio of a peak of the sample to be measured and a peak of the reference substance is calculated in advance. The compositional ratios of the liquid crystal compounds in the liquid crystal composition can be accurately obtained by correcting by using the relative intensity of the peak areas of the component compounds with respect to the reference substance.

Sample of Liquid Crystal Compound for Measuring Characteristics:

A sample of the liquid crystal compound for measuring characteristics includes two cases, i.e., the case where the compound itself is used as a sample, and the case where the compound is mixed with mother liquid crystals to prepare a sample.

In the later case where a sample is prepared by mixing the compound with mother liquid crystals, the measurement is carried out in the following manner. A sample was produced by mixing 15% by weight of the compound and 85% by weight of mother liquid crystals. A value of characteristics of the compound was calculated by extrapolating from a value obtained by measurement.

Extrapolated Value=(100×(measured value of sample)−(percentage by weight of mother liquid crystals)×(value measured for mother liquid crystals))/(percentage by weight of liquid crystal compound)

In the case where a smectic phase was exhibited at 25° C. or crystals were deposited at 25° C. at this ratio of the liquid crystal compound and the mother liquid crystals, the ratio of the compound and the mother liquid crystals was changed step by step in the order of (10% by weight/90% by weight), (5% by weight/95% by weight), (1% by weight/99% by weight), respectively. The value of characteristics of the sample was measured at a ratio where a smectic phase or crystals were not deposited at 25° C., and an extrapolated value was obtained by the aforementioned equation, which was designated as a value of characteristics of the liquid crystal compound.

While there are various kinds of mother liquid crystals for the aforementioned measurement, the composition of the mother liquid crystals i was as follows, for example.

Mother Liquid Crystals i:

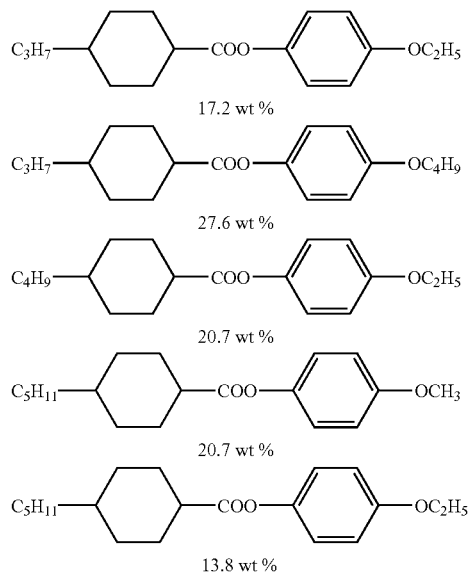

As a sample for measuring characteristics of a liquid crystal composition, the liquid crystal composition itself was used.

Measurement Method of Characteristics of Liquid Crystal Compound:

Measurement of the characteristics was carried out according to the following methods. Most methods are described in the Standard of Electric Industries Association of Japan, EIAJ ED-2521A or those with some modifications. A TFT was not attached to a TN device or a VA device used for measurement.

Among the measured values, the values obtained with the liquid crystal compound itself as a sample and the values obtained with the liquid crystal composition itself as a sample were described as experimental data. In the case where the values were obtained with the mixture of the compound with the mother liquid crystals, the extrapolated values were described as experimental data.

Phase Structure and Phase Transition Temperature (° C.):

The measurement was carried out in the methods (1) and (2) below.

(1) A compound was placed on a hot plate (Hot Stage Model FP-52, produced by Mettler Co., Ltd.) in a melting point apparatus equipped with a polarizing microscope, and while heating at the rate of 3° C. per minute, the state of the phase and the changes thereof were observed with the polarizing microscope to determine the kind of the phase.

(2) A sample was heated and cooled at a rate of 3° C. per minute by using a scanning calorimeter, DSC-7 System or Diamond DSC System, produced by Perkin-Elmer, Inc., whereby a starting point of an endothermic peak or an exothermic peak associated with phase change of the sample was obtained by extrapolation (on set) to determine phase transition temperature.

In the following description, a crystal is denoted by "Cr". In the case where a crystal is distinguished into two crystals, they are denoted by "$C_1$" and "$C_2$", respectively. A smectic phase is denoted by "S", and a nematic phase is denoted by "N." A liquid (isotropic phase) is denoted by "Iso". In the case where a smectic phase is distinguished into a smectic B phase and a smectic A phase, they are denoted by "$S_B$" and "$S_A$", respectively. The expression of the phase transition temperature, "C 50.0 N 100.0 Iso", for example, means that the transition temperature of from a crystal to a nematic phase (CN) is 50.0° C., and the transition temperature of from a nematic phase to a liquid (NI) is 100.0° C. The other expressions are applied with the same rule.

Maximum Temperature of Nematic Phase (NI; ° C.):

A sample was placed on a hot plate in a melting point apparatus equipped with a polarizing microscope, and while heating at the rate of 1° C. per minute, was observed with the polarizing microscope. A temperature where a part of the sample is changed from a nematic phase to an isotropic liquid was measured. The maximum temperature of a nematic phase may be abbreviated to "a maximum temperature" in some cases.

Minimum Temperature of Nematic Phase (Tc; ° C.):

The glass bottles containing a sample having a nematic phase were stored in a freezer at 0° C., −10° C., −20° C., −30° C., −40° C. for a prescribed period of time. For example, a sample at −20° C. remains a nematic phase. When a sample changes to crystal of smectic phase at 30° C. Tc is expressed as ≦−20° C. The minimum temperature of a nematic phase may be abbreviated to "a minimum temperature".

Viscosity (η; measured at 20° C.; mPa·s):

The viscosity was measured by means of an E-type viscometer.

Optical Anisotropy (refractive index anisotropy; Δn; measured at 25° C.):

Measurement was carried out with an Abbe refractometer mounting a polarizing plate on an ocular using a light at a wavelength of 589 nm. The surface of a main prism was rubbed in one direction, and then a sample was dropped on the main prism. Refractive index (n∥) was measured when the direction of a polarized light was parallel to that of the rubbing. Refractive index (n⊥) was measured when the direction of a polarized light was perpendicular to that of the rubbing. A value of optical anisotropy was calculated from the equation: Δn=n∥−n⊥.

Dielectric Anisotropy (Δ∈; measured at 25° C.):

A sample was put in a TN device having a distance between two glass substrates (cell gap) of 9 μm and a twist angle of 80°. Sine waves (10 V 1 kHz) were applied to the device, and a dielectric constant (∈∥) in a major axis direction of a liquid crystal molecule was measured after 2 seconds. Sine waves (0.5 V, 1 kHz) were applied to the device, and a dielectric constant ($\epsilon\perp$) in a minor axis direction of a liquid crystal molecule was measured after 2 seconds. A value of a dielectric anisotropy was calculated from the equation: $\Delta\epsilon=\epsilon\|-\epsilon\perp$.

Threshold Voltage (Vth; measured at 25° C.; V):

Measurement was carried out with an LCD Evaluation System Model LCD-5100 made by Otsuka Electronics Co., Ltd. The light source was a halogen lamp. A sample was poured into a VA device of a normally black mode, and the device was sealed with UV curable adhesive. Voltage to be applied to the device (60 Hz, rectangular waves) was stepwise increased by 0.02V starting from 0V up to 20V. During the stepwise increasing, the device was irradiated with light in a perpendicular direction, and an amount of the light passing through the device was measured. Voltage-transmission curve was prepared, in which a maximum amount of a light corresponded to 100% transmittance, and a minimum amount of a light corresponded to 0% transmittance. Threshold voltage is a value at 10% transmittance.

Voltage Holding Ratio (VHR-1; measured at 25° C.; %):

A TN device used for measurement has a polyimide-alignment film and the cell gap between two glass plates is 5 μm. A sample was poured into the device, and then the device was sealed with an adhesive which is polymerized by the irradiation of an ultraviolet light. The TN device was applied and charged with pulse voltage (60 microseconds at 5V). Decreasing voltage was measured for 16.7 milliseconds with High Speed Voltmeter and the area A between a voltage curve and a horizontal axis in a unit cycle was obtained. The area B was an area without decreasing. Voltage holding ratio is a percentage of the area A to the area B.

Voltage Holding Ratio (VHR-2; measured at 80° C.; %):

A TN device used for measurement has a polyimide-alignment film and the cell gap between two glass plates is 5 μm. A sample was poured into the device, and then the device was sealed with an adhesive which is polymerized by the irradiation of an ultraviolet light. The TN device was applied and charged with pulse voltage (60 microseconds at 5V). Decreasing voltage was measured for 16.7 milliseconds with High Speed Voltmeter and the area A between a voltage curve and a horizontal axis in a unit cycle was obtained. The area B was an area without decreasing. Voltage holding ratio is a percentage of the area A to the area B.

Voltage Holding Ratio (VHR-3; measured at 25° C.; %):

A voltage holding ratio was measured after irradiating with ultraviolet light to evaluate stability to ultraviolet light. A composition having large VHR-3 has a large stability to ultraviolet light. A TN device used for measurement has a polyimide-alignment film and the cell gap is 5 μm. A sample was poured into the device, and then the device was irradiated with light for 20 minutes. The light source was a superhigh voltage mercury lamp USH-500D (produced by Ushio, Inc.), and the distance between the device and the light source is 20 cm. In measurement of VHR-3, a decreasing voltage is measured for 16.7 milliseconds. VHR-3 is desirably 90% or more, and more desirably 95% or more.

Voltage Holding Ratio (VHR-4; measured at 25° C.; %):

A voltage holding ratio was measured after heating a TN device having a sample poured therein in a constant-temperature bath at 80° C. for 500 hours to evaluate stability to heat. A composition having large VHR-4 has a large stability to heat. In measurement of VHR-4, a decreasing voltage is measured for 16.7 milliseconds.

Response Time (τ; measured at 25° C.; millisecond):

Measurement was carried out with an LCD Evaluation System Model LCD-5100 made by Otsuka Electronics Co., Ltd. Light source is a halogen lamp. Low-pass filter was set at 5 kHz. A sample was poured into a VA device of a normally black mode, in which a rubbing direction is anti-parallel. The device was sealed with UV curable adhesive, rectangle waves (60 Hz, 10V, 0.5 seconds) were applied thereto. During application, the device was irradiated with light in a perpendicular direction, and an amount of the light passing through the device was measured. A maximum amount of a light corresponds to 100% transmittance, and a minimum amount of a light corresponds to 0% transmission. Fall time (τr; millisecond) is a period of time required for the change in transmittance from 90% to 10%.

TABLE 3

Method of Description of Compound using Symbols
$R\text{-}(A_1)\text{-}Z_1\text{-}\ldots\text{-}Z_n\text{-}(A_n)\text{-}R'$

| 1) Left Terminal Group | Symbol |
|---|---|
| $C_nH_{2n+1}—$ | n- |
| $C_nH_{2n+1}O—$ | nO- |
| $C_mH_{2m+1}OC_nH_{2n}—$ | mOn- |
| $CH_2=CH—$ | V- |
| $C_nH_{2n+1}—CH=CH—$ | nV- |
| $CH_2=CH—C_nH_{2n}—$ | Vn- |
| $C_mH_{2m+1}—CH=CH—C_nH_{2n}$ | mVn- |
| $CF_2=CH—$ | VFF- |
| $CF_2=CH—C_nH_{2n}—$ | VFFn- |

| 2) Right Terminal Group | Symbol |
|---|---|
| $—C_nH_{2n+1}$ | -n |
| $—OC_nH_{2n+1}$ | -On |
| $—CH=CH_2$ | -V |
| $—CH=CH—C_nH_{2n+1}$ | -Vn |
| $—C_nH_{2n}—CH=CH_2$ | -nV |
| $—CH=CF_2$ | -VFF |

| 3) Bonding group -Zn- | Symbol |
|---|---|
| $—C_2H_4—$ | 2 |
| $—COO—$ | E |
| $—CH=CH—$ | V |
| $—C\equiv C—$ | T |
| $—CF_2O—$ | X |
| $—OCF_2—$ | x |
| $—C_2H_4CF_2O—$ | 2X |
| $—C_2H_4OCF_2—$ | 2x |
| $—CH_2O—$ | 1O |
| $—OCH_2—$ | O1 |

| 4) Ring Structure -$A_n$- | Symbol |
|---|---|
| 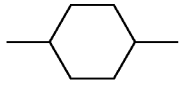 | H |
| 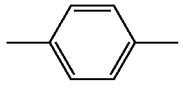 | B |
| 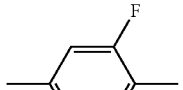 | B(F) |
| 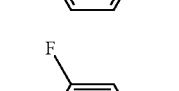 | B(2F) |

TABLE 3-continued

Method of Description of Compound using Symbols
$R-(A_1)-Z_1- \ldots -Z_n-(A_n)-R'$

| Structure | Symbol |
|---|---|
| (2,3-difluorophenylene) | B(2F, 3F) |
| (2-trifluoromethylphenylene) | B(2CF3) |
| (2-difluoromethyl-3-fluorophenylene) | B(2CF2H, 3F) |
| (2,5-difluorophenylene) | B(2F, 5F) |

5) Example of Description

Example 1 V2-BB(F)B-1

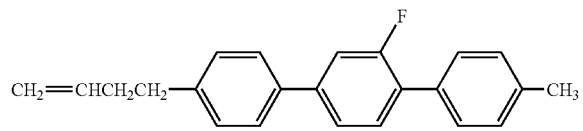

Example 2 3-HB(2F, 3F)-O2

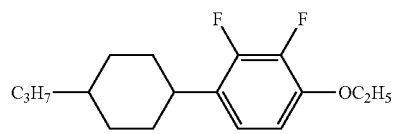

Example 3 3-HHB-1

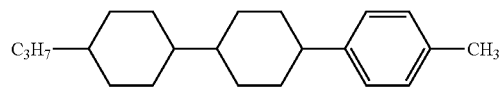

Example 4 5-HBB(F)B-3

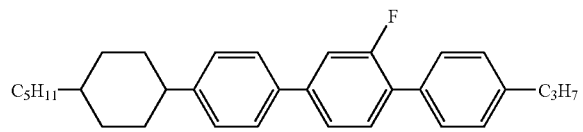

Specific Resistance (ρ; measured at 25° C.; Ωcm):

1.0 ml of a sample was charged in a vessel equipped with electrodes. A direct current voltage of 10V was applied to the vessel, and after lapsing 10 second from the application of voltage, the direct electric current was measured. The specific resistance was calculated by the equation:

(specific resistance)=((voltage)×(electric capacity of vessel))/((direct current)×(dielectric constant of vacuum))

The invention will be explained in detail by way of Examples. The invention is not limited by the Examples described below. The compounds described in the Comparative Examples and the Examples are expressed by the symbols according to the definition in Table 3. In Table 3, the configuration of 1,4-cyclohexylene is trans. The parenthesized number next to the symbolized compounds in the Examples corresponds to the number of the desirable compound. The symbol (−) means other liquid crystal compound. A ratio (percentage) of a liquid crystal compound is percentage by weight (% by weight) based on the total weight of liquid crystal compounds, and the liquid crystal compositions further contain impurities. Last, the characteristics of the composition are summarized.

Example 1

Synthesis of 4'-ethoxy-2,3,2',3'-tetrafluoro-4-(4'-vinylbicyclohexyl-4-ylmethoxy)-biphenyl (a7)

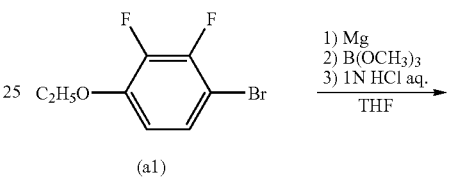

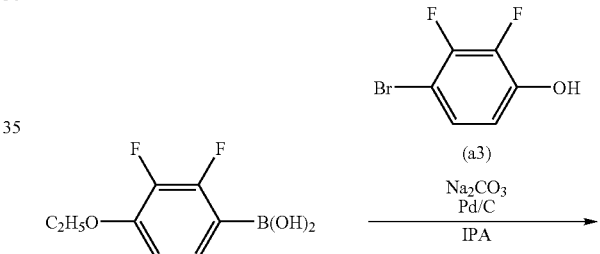

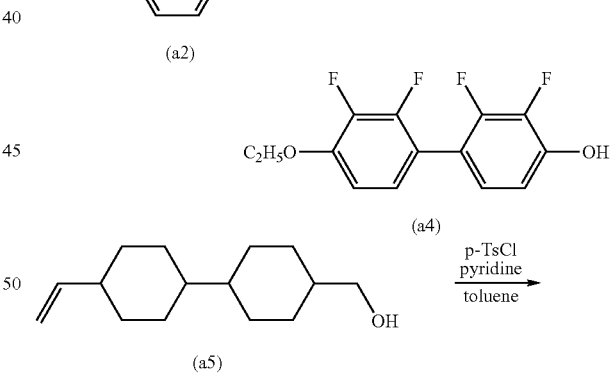

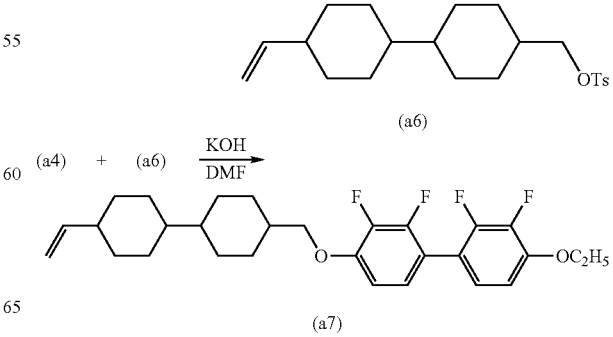

First Step

In a reactor under nitrogen atmosphere, 50 ml of tetrahydrofuran (THF) was added to 6.15 g of magnesium (Mg), followed by stirring at 44° C. 60.0 g of 1-bromo-4-etoxy-2,3-difluorobenzene (a1) dissolved in 130 ml of THF was added dropwise thereto in the temperature range of 38° C. to 49° C. for 1 hour. The resulting solution was added dropwise to a solution of 200 ml of THF and 39.5 g of trimethyl boratein the temperature range of −50° C. to −30° C. The reaction solution was injected into a mixture of 500 ml of 1N hydrochloric acid and 600 ml of ethyl acetate. The mixture was separated into organic layer and aqueous layer, and the organic layer was extracted. The resulting organic layer was washed with saturated chloride aqueous solution and dried over anhydrous magnesium sulfate, and the solvent was concentrated under reduced pressure to provide the residue. The resulting residue was purified by re-crystallization from a heptane, dried to provide 41.6 g of 4-ethoxy-2,3-difluorophenylboronic acid (a2) as a yellow solid.

Second Step

In a reactor under nitrogen atmosphere, 20.0 g of compound (a2)17.2 g of 4-bromo-2,3-difluorophenol (a3), 30.6 g of sodium carbonate, 0.54 g of palladium on carbon catalyst (Pd/C) were dissolved in 120 mL of 2-propanol (IPA). After stirring by refluxing for 10 hours, the reaction mixture was cooled to room temperature, and injected into a mixture of 500 ml of 1N hydrochloric acid and 300 ml of toluene which was cooled into 0° C. The mixture was separated into organic layer and aqueous layer and the organic layer was extracted. The resulting organic layer was washed with saturated chloride aqueous solution and dried over anhydrous magnesium sulfate, and the solvent was concentrated under reduced pressure to provide the residue. The resulting residue was purified by recrystallization from heptan, dried to provide 13.2 g of 4'-ethoxy-2,3,2',3'-tetrafluorobiphenyl-4-ol (a4) as a white solid.

Third Step

In a reactor under nitrogen atmosphere, 20.0 g of (4'-vinylbicyclohexyl-4-yl)-methanol (a5) was added into 100 ml of pyridine, followed by stirring at 5° C. The solution in which 34.3 g of p-p-toluenesulfonyl chloride (p-TsCl) was dissolved in 50 ml of toluene was added dropwise to the resulting solution, followed by stirring at room temperature for 20 hours. The resulting reaction mixture was injected into a mixture of 200 ml of the water cooled to 0° C. and 200 ml of toluene. The mixture was separated into organic layer and aqueous layer, and the organic layer was extracted. The resulting organic layer was washed with water and dried over anhydrous magnesium sulfate, and the solvent was concentrated under reduced pressure to provide the residue. The resulting residue was purified by column chromatography (silica gel; toluene). The solvent was concentrated under reduced pressure to provide 32.1 g of 4'-vinylbicyclohexyl-4-ylmethltoluene-4-sulfonic acid (a6) as a white solid.

Fourth step

In a reactor under nitrogen atmosphere, 4.0 g of compound (a4), 5.3 g of compound (a6) and 1.2 g of potassium hydroxide (KOH) were added into 30 ml of N,N-dimethylformamide (DMF), followed by stirring at 60° C. for 14 hours. The reaction solution was cooled to 30° C., to which 100 ml of water and 100 ml of toluene were added. The mixture was separated into organic layer and aqueous layer and the organic layer was extracted. The resulting organic layer was separated and washed with water and dried over anhydrous magnesium sulfate. The solvent was distilled off under reduced pressure to provide the residue. The resulting residue was purified by column chromatography (silica gel; toluene), further purified by recrystallization from (volume ratio Sol-mix A-11: toluene=1:2), dried to provide 2.5 g of 4'-ethoxy-2,3,2',3'-tetrafluoro-4-(4'-vinylbicyclohexyl-4-ylmetoxy)-biphenyl (a7).

The chemical shifts δ (ppm) in $^1$H-NMR analysis were as follows, and thus the resulting compound was identified as 4'-etoxy-2,3,2',3'-tetrafluoro-4-(4'-vinylbicyclohexyl-4-yl-metoxy)-biphenyl (a7). The solvent for measurement was CDCl$_3$.

Chemical shift δ (ppm): 7.03-6.98(m, 2H), 6.81-6.76(m, 2H), 5.81-5.74(m, 1H), 4.98-4.94(d, 1H), 4.89-4.87(d, 1H), 4.16(q, 2H), 3.86(d, 2H), 1.96-1.77(m, 10H), 1.48(t, 3H) 1.09-1.02(m, 10H).

The resulting compound (a7) had phase transition temperatures (° C.) of Cr 131.5 N 230.1 Iso.

Example 2

Synthesis of 4'-ethoxy-2,3,2',3'-tetrafluoro-4-(trans-4-vinylcyclohexylmethoxy)-biphenylmethoxy)-biphenyl (a10)

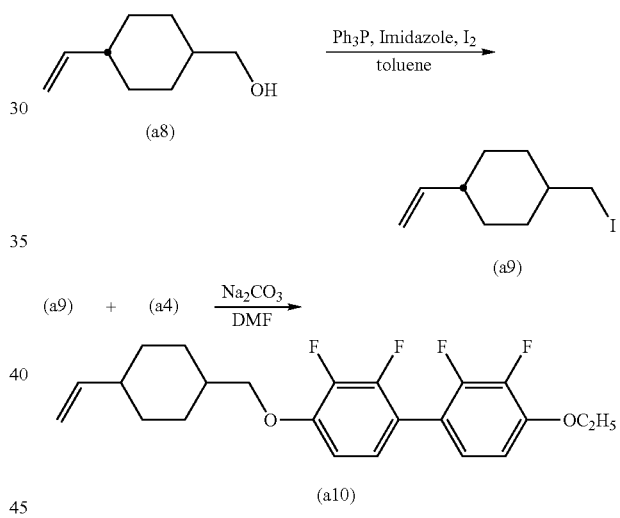

First Step

In a reactor under nitrogen atmosphere, 200 ml of toluene was added to 12.0 g of compounds (a8), 7.6 g of imidazole and 29.2 g of triphenylphosphine (Ph$_3$P), followed by stirring at 5° C. 27.2 g of iodine divided by 10 parts were added thereto in the temperature range of 5° C. to 10° C., followed by stirring for three hours to verify the completion of reaction by GC analysis. The resulting reaction mixture was filtered to remove deposited solid matters, and the solvent was distilled off from the resulting filtered solution under reduced pressure. The resulting residue was purified by column chromatography (heptane, silica gel), dried to provide 15.2 g of 1-iodidemethyl-trans-4-vinylcyclohexane (a9). The compounds (a8) can be produced according to the synthesis methods described in International publication No. 2006/064853.

Second step

In a reactor under nitrogen atmosphere, 4.4 g of compound (a4) and 3.2 g of sodium carbonate were added into 20 ml of DMF, followed by stirring at 80° C. 3.8 g of compound (a9) was added thereto, followed by stirring at 80° C. for an hour.

The resulting reaction mixture was cooled to 30° C., to which 30 ml of water and 30 ml of toluene were added. The mixture was separated into organic layer and aqueous layer and the organic layer was extracted. The resulting organic layer was separated and washed with salt water and dried over anhydrous magnesium sulfate. The solvent was distilled off under reduced pressure to provide the residue. The resulting residue was purified by column chromatography (volume ratio heptane: toluene=4:1), further by recrystallization from the solvent mixture of Solmix A-11 and heptane (volume ratio Solmix A-11: heptane=1:2), dried to provide 1.8 g of 4'-ethoxy-2,3,2',3'-tetrafluoro-4-(trans-4-vinylcyclohexylmethoxy)-biphenylmethoxy)-biphenyl (a10).

The chemical shifts δ (ppm) in $^1$H-NMR analysis were as follows, and thus the resulting compound was identified as 4'-ethoxy-2,3,2',3'-tetrafluoro-4-(trans-4-vinylcyclohexyl-metoxy)-biphenylmethoxy)-biphenyl. The solvent for measurement was CDCl$_3$.

Chemical shift δ (ppm): 7.03-6.99(m, 2H), 6.81-6.77(m, 2H), 5.83-5.76(m, 1H), 5.02-4.97(d, 1H), 4.93-4.92(d, 1H), 4.16(q, 2H), 3.88(d, 2H), 1.98-1.96(m, 3H), 1.49(t, 3H)-1.22-1.10(m, 4H).

The resulting compound (a10) had phase transition temperatures (° C.) of Cr 66.4 N 104.8 Iso.

Comparative Example 1

Example 12 was selected from the compositions disclosed in JP 2007-2132 A. The basis is that the composition contains compounds (1) and (3). The components and characteristics of the composition were as follows. The compositions were prepared and measured according to the methods described above, because the response time at 25° C. was not described.

| | | |
|---|---|---|
| 3-HB(F)-3 | (—) | 2% |
| 3-HHB(2F)-1 | (3) | 3% |
| 3-HHB(2F)-2 | (3) | 4% |
| 3-HHB(F)-O2 | (3) | 3% |
| 3-HBB(F)-O2 | (3) | 3% |
| 3-HH1OB(2F)-O2 | (3) | 3% |
| 3-HxB(2F,3F)-1 | (—) | 8% |
| 3-H2XB(2F,3F)-O1 | (—) | 12% |
| 3-H1OB(2F,3F)B(2F,3F)-O2 | (1) | 2% |
| 3-HO1(2F,3F)B(2F,3F)-O2 | (—) | 2% |
| 3-HXB(2CF3)B(2F,3F)-O1 | (—) | 1% |
| 3-HXB(2F)B(2F,3F)-O1 | (—) | 3% |
| 3-HxB(F)B(2F,3F)-O1 | (—) | 6% |
| 3-H2xB(2F,3F)B(2F,3F)-1 | (—) | 4% |
| 3-HB2B(2CF2H,3F)B-O2 | (—) | 1% |
| 3-HB1OB(2CF2H,3F)B-O2 | (—) | 2% |
| 5-HBO1B(2CF2H,3F)B-1 | (—) | 1% |
| 3-HXB(2F,3F)B-O2 | (—) | 1% |
| 3-HxB(2F,3F)B-O1 | (—) | 1% |
| 3-HHxB(2F,3F)-O1 | (—) | 4% |
| 3-HH2XB(2F,3F)-1 | (—) | 6% |
| 3-HB(2F,3F)XB(2F,3F)-1 | (—) | 4% |
| 3-HB2XB(2F,3F)-O1 | (—) | 10% |
| 3-HB2xB(2F,3F)-O2 | (—) | 10% |
| 3-HB(2F,3F)2xB(2F,3F)-O1 | (—) | 4% |

NI = 100.0° C.;
Tc ≤ −20° C.;
Δn = 0.109;
η = 50.0 mPa · s;
Δε = −4.3;
τ = 25.3 ms.

Example 3

The compositions of Example 3 have a smaller viscosity and a shorter response time than those of Comparative Example 1.

| | | |
|---|---|---|
| 3-HH1OB(2F,3F)B(2F,3F)-O4 | (1) | 4% |
| 5-HH1OB(2F,3F)B(2F,3F)-O4 | (1) | 3% |
| 3-HHEB(2F,3F)B(2F,3F)-O4 | (1) | 3% |
| 5-HHEB(2F,3F)B(2F,3F)-O2 | (1) | 3% |
| 3-HEB(2F,3F)B(2F,3F)-O2 | (1) | 6% |
| 5-HEB(2F,3F)B(2F,3F)-O2 | (1) | 4% |
| V-H1OB(2F,3F)B(2F,3F)-O4 | (1-1-3) | 3% |
| V-HH-3 | (2-1-1) | 42% |
| 1V-HH-3 | (2-1-1) | 6% |
| 7-HB-1 | (2-2-1) | 4% |
| V2-BB-1 | (2-3-1) | 6% |
| 3-HB(2F,3F)-O2 | (4-1-1) | 8% |
| 5-HB(2F,3F)-O2 | (4-1-1) | 8% |

NI = 74.4° C.;
Tc ≤ −20° C.;
Δn = 0.086;
η = 17.6 mPa · s;
Δε = −3.3;
Vth = 2.16 V;
τ = 7.2 ms;
VHR-1 = 99.1%;
VHR-2 = 98.2%;
VHR-3 = 98.2%.

Example 4

The compositions of Example 4 have a smaller viscosity and a shorter response time than those of Comparative Example 1.

| | | |
|---|---|---|
| 3-HH1OB(2F,3F)B(2F,3F)-O4 | (1) | 3% |
| 5-HH1OB(2F,3F)B(2F,3F)-O4 | (1) | 3% |
| 3-H1OB(2F,3F)B(2F,3F)-O4 | (1) | 4% |
| 5-H1OB(2F,3F)B(2F,3F)-O4 | (1) | 3% |
| V-HH1OB(2F,3F)B(2F,3F)-O4 | (1-1-1) | 3% |
| V-HH-3 | (2-1-1) | 31% |
| 3-HB-O2 | (2-2-1) | 4% |
| V-HHB-1 | (3-1-1) | 9% |
| 3-BB(F)B-2V | (3-3-1) | 3% |
| V-HB(2F,3F)-O2 | (4-1-1) | 8% |
| V-HB(2F,3F)-O4 | (4-1-1) | 10% |
| 3-H2B(2F,3F)-O2 | (4-2-1) | 5% |
| V-HHB(2F,3F)-O2 | (4-4-1) | 7% |
| V-HHB(2F,3F)-O4 | (4-4-1) | 7% |

NI = 76.6° C.;
Tc ≤ −20° C.;
Δn = 0.093;
η = 24.5 mPa · s;
Δε = −3.0;
Vth = 2.29 V;
τ = 8.9 ms;
VHR-1 = 99.1%;
VHR-2 = 98.3%;
VHR-3 = 98.2%.

Example 5

The compositions of Example 5 have a smaller viscosity and a shorter response time than those of Comparative Example 1.

| 3-HHEB(2F,3F)B(2F,3F)-O4 | (1) | 4% |
|---|---|---|
| 5-HHEB(2F,3F)B(2F,3F)-O2 | (1) | 3% |
| 3-HEB(2F,3F)B(2F,3F)-O4 | (1) | 5% |
| 5-HEB(2F,3F)B(2F,3F)-O2 | (1) | 4% |
| V-HH-3 | (2-1-1) | 28% |
| V-HH-5 | (2-1-1) | 7% |
| 3-HHB-1 | (3-1-1) | 6% |
| 2-BB(F)B-3 | (3-3-1) | 4% |
| 3-HHEH-3 | (3-8) | 3% |
| 3-HHEH-5 | (3-8) | 3% |
| V-HHB(2F,3F)-O2 | (4-4-1) | 10% |
| V-HHB(2F,3F)-O4 | (4-4-1) | 10% |
| 2-HBB(2F,3F)-O2 | (4-6-1) | 5% |
| 3-HBB(2F,3F)-O2 | (4-6-1) | 8% |

NI = 87.3° C.;
Tc ≤ −20° C.;
Δn = 0.098;
η = 25.6 mPa · s;
Δε = −2.9;
Vth = 2.38 V;
τ = 9.2 ms;
VHR-1 = 99.2%;
VHR-2 = 98.0%;
VHR-3 = 98.3%.

Example 6

| 3-H1OB(2F,3F)B(2F,3F)-O4 | (1) | 4% |
|---|---|---|
| V-HHEB(2F,3F)B(2F,3F)-O4 | (1-1-2) | 5% |
| V-HEB(2F,3F)B(2F,3F)-O4 | (1-1-4) | 5% |
| 2-HH-3 | (2-1-1) | 7% |
| 3-HH-O1 | (2-1-1) | 5% |
| V-HH-3 | (2-1-1) | 30% |
| 1V-HBB-2 | (3-2-1) | 3% |
| 3-HHEBH-5 | (3-4-1) | 3% |
| 3-HB(F)BH-5 | (3-6-1) | 3% |
| 3-H1OB(2F,3F)-O2 | (4-3-1) | 7% |
| 3-H1OB(2F,3F)-O4 | (4-3-1) | 7% |
| 5-H1OB(2F,3F)-O2 | (4-3-1) | 6% |
| 3-HH1OB(2F,3F)-O2 | (4-5-1) | 8% |
| 3-HH1OB(2F,3F)-O2 | (4-5-1) | 7% |

NI = 72.1° C.;
Tc ≤ −20° C.;
Δn = 0.98;
η = 24.1 mPa · s;
Δε = −3.2;
Vth = 2.19 V;
τ = 8.9 ms;
VHR-1 = 99.1%;
VHR-2 = 98.1%;
VHR-3 = 98.0%.

Example 7

| 3-H1OB(2F,3F)B(2F,3F)-O4 | (1) | 3% |
|---|---|---|
| 5-H1OB(2F,3F)B(2F,3F)-O4 | (1) | 3% |
| 5-HH1OB(2F,3F)B(2F,3F)-O4 | (1) | 3% |
| V-HH-3 | (2-1-1) | 25% |
| 1V-HH-3 | (2-1-1) | 7% |
| 5-BB-1 | (2-3-1) | 3% |
| V2-BB(F)B-3 | (3-3-1) | 3% |
| 3-HBBH-5 | (3-5-1) | 3% |
| 5-HBB(F)B-3 | (3-7-1) | 6% |
| V-HB(2F,3F)-O2 | (4-1-1) | 10% |
| V-HB(2F,3F)-O4 | (4-1-1) | 10% |
| 5-BB(2F,3F)-O2 | (4-7) | 5% |
| 3-HBB(2F,3F)-O2 | (4-6-1) | 10% |
| 5-HBB(2F,3F)-O2 | (4-6-1) | 9% |

NI = 82.2° C.;
Tc ≤ −20° C.;
Δn = 0.113;
η = 25.7 mPa · s;
Δε = −2.9;
Vth = 2.31 V;
τ = 9.1 ms;
VHR-1 = 99.1%;
VHR-2 = 98.2%;
VHR-3 = 98.1%.

Example 8

| 3-H1OB(2F,3F)B(2F,3F)-O4 | (1) | 3% |
|---|---|---|
| 5-H1OB(2F,3F)B(2F,3F)-O4 | (1) | 3% |
| 2-HH-3 | (2-1-1) | 28% |
| 3-HH-O1 | (2-1-1) | 13% |
| 3-HB-O2 | (2-2-1) | 8% |
| V-HHB(2F,3F)-O2 | (4-4-1) | 10% |
| 3-HBB(2F,3F)-O2 | (4-6-1) | 11% |
| 5-HBB(2F,3F)-O2 | (4-6-1) | 11% |
| 3-HH2B(2F,3F)-O2 | (4-8) | 9% |
| 1O1-HBBH-5 | (—) | 4% |

NI = 90.0° C.;
Tc ≤ −20° C.;
Δn = 0.093;
η = 21.8 mPa · s;
Δε = −2.8;
Vth = 2.44 V;
τ = 8.2 ms;
VHR-1 = 99.1%;
VHR-2 = 98.2%;
VHR-3 = 98.1%.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A liquid crystal composition having a negative dielectric anisotropy, comprising two components, wherein the first component is at least one compound selected from the group of compounds represented by formula (1), and the second component is at least one compound selected from the group of compounds represented by formula (2):

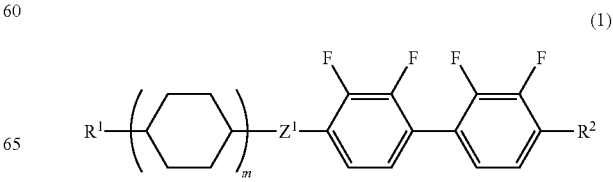

-continued

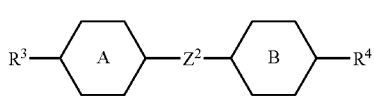
(2)

wherein $R^1$, $R^2$, $R^3$ and $R^4$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine; ring A and ring B are each independently 1,4-cyclohexylene or 1,4-phenylene; $Z^1$ is methyleneoxy or carbonyloxy; $Z^2$ is a single bond, ethylene, vinylene, methyleneoxy or carbonyloxy; and m is 1 or 2.

2. The liquid crystal composition according to claim 1, wherein the first component is at least one compound selected from the group of compounds represented by formula (1-1):

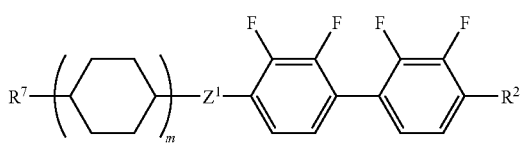
(1-1)

wherein $R^7$ is alkenyl having 2 to 12 carbons; $R^2$ is alkyl having 1 to 12 carbons, alkoxy having 1 to 12 carbons or alkenyl having 2 to 12 carbons or alkenyl having 2 to 12 carbons in which arbitrary hydrogen is replaced by fluorine; and $Z^1$ is methyleneoxy or carbonyloxy, and m is 1 or 2.

3. The liquid crystal composition according to claim 1, wherein the second component is at least one compound selected from the group of compounds represented by formula (2-1) to (2-3):

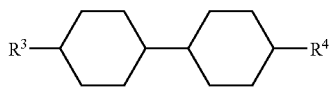
(2-1)

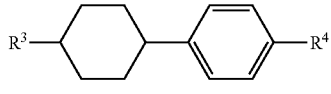
(2-2)

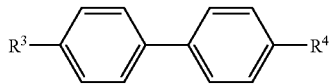
(2-3)

wherein $R^3$ and $R^4$ are each independently alkyl having 1 to 12 carbons, alkoxy having 1 to 12 carbons or alkenyl having 2 to 12 carbons or alkenyl having 2 to 12 carbons in which arbitrary hydrogen is replaced by fluorine.

4. The liquid crystal composition according to claim 3, wherein the second component is at least one compound selected from the group of compounds represented by formula (2-1).

5. The liquid crystal composition according to claim 3, wherein the second component is a mixture of at least one compound selected from the group of compounds represented by formula (2-1) and at least one compound selected from the group of compounds represented by formula (2-3).

6. The liquid crystal composition according to claim 1, a ratio of the first component is from approximately 5% by weight to approximately 40% by weight, a ratio of the second component is from approximately 25% by weight to approximately 70% by weight.

7. The liquid crystal composition according to claim 1, wherein the composition further comprises at least one compound selected from the group of compound represented by formula (3) as a third component:

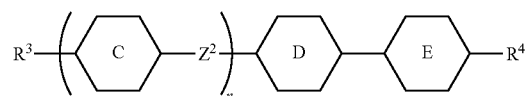
(3)

wherein $R^3$ and $R^4$ are each independently alkyl having 1 to 12 carbons, alkoxy having 1 to 12 carbons, alkenyl having 2 to 12 carbons, or alkenyl having 2 to 12 carbons in which arbitrary hydrogen is replaced by fluorine ;ring C, ring D and ring E are each independently 1,4-cyclohexylene, 1,4-phenylene, 2-fluoro-1,4-phenylene or 2, 5-difluoro-1,4-phenylene; $Z^2$ is independently a single bond, ethylene, vinylene, methyleneoxy or carbonyloxy; and n is 1 or 2.

8. The liquid crystal composition according to claim 7, wherein the third component is at least one compound selected from the group of compounds represented by formula (3-1) to (3-7):

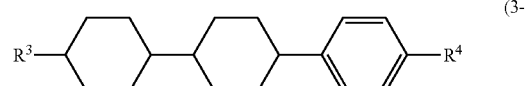
(3-1)

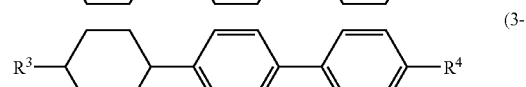
(3-2)

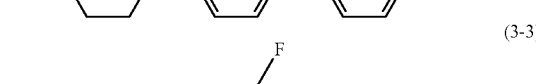
(3-3)

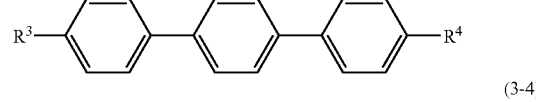
(3-4)

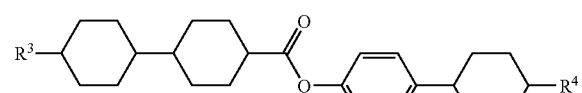
(3-5)

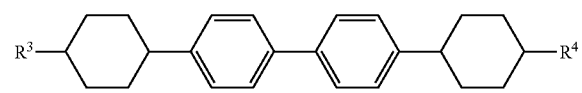
(3-6)

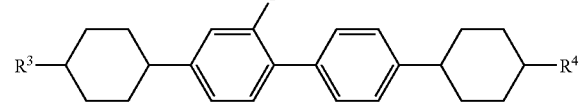
(3-7)

wherein $R^3$ and $R^4$ are each independently alkyl having 1 to 12 carbons, alkoxy having 1 to 12 carbons, alkenyl having 2 to 12 carbons, or alkenyl having 2 to 12 carbons in which arbitrary hydrogen is replaced by fluorine.

9. The liquid crystal composition according to claim 8, wherein the third component is at least one compound selected from the group of compounds represented by formula (3-1).

10. The liquid crystal composition according to claim 8, wherein the third component is at least one compound selected from the group of compounds represented by formula (3-3).

11. The liquid crystal composition according to claim 8, wherein the third component is a mixture of at least one compound selected from the group of compounds represented by formula (3-1) and at least one compound selected from the group of compounds represented by formula (3-3).

12. The liquid crystal composition according to claim 7, wherein a ratio of the third component is from approximately 5% by weight to approximately 30% by weight based on the total weight of the liquid crystal composition.

13. The liquid crystal composition according to claim 1, wherein the composition further comprises at least one compound selected from the group of compounds represented by formula (4) as a fourth component:

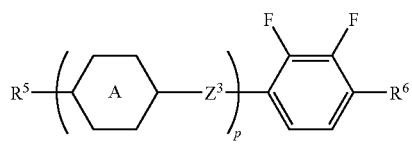
(4)

wherein $R^5$ and $R^6$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine; ring A is independently 1,4-cyclohexylene or 1,4-phenylene; $Z^3$ is independently a single bond, ethylene, methyleneoxy or carbonyloxy; and p is 1, 2 or 3.

14. The liquid crystal composition according to claim 13, wherein the fourth component is at least one compound selected from the group of compounds represented by formulas (4-1) to (4-6):

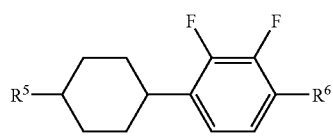
(4-1)

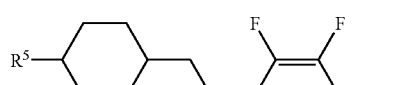
(4-2)

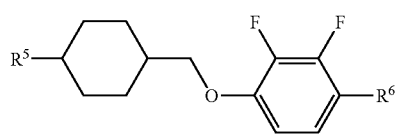
(4-3)

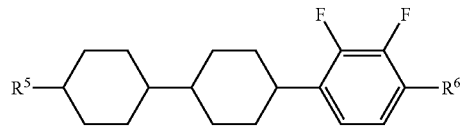
(4-4)

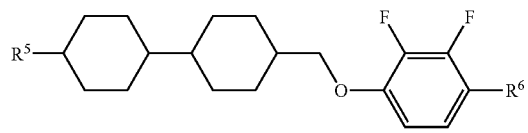
(4-5)

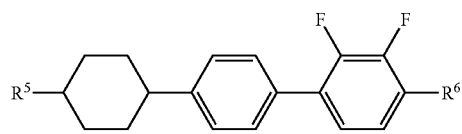
(4-6)

wherein $R^5$ and $R^6$ are each independently alkyl having 1 to 12 carbons, alkoxy having 1 to 12 carbons, alkenyl having 2 to 12 carbons or alkenyl having 2 to 12 carbons in which arbitrary hydrogen is replaced by fluorine.

15. The liquid crystal composition according to claim 14, wherein the fourth component is at least one compound selected from the group of compounds represented by formula (4-1).

16. The liquid crystal composition according to claim 14, wherein the fourth component is a mixture of at least one compound selected from the group of compounds represented by formula (4-1) and at least one compound selected from the group of compounds represented by formula (4-4).

17. The liquid crystal composition according to claim 14, wherein the fourth component is a mixture of at least one compound selected from the group of compounds represented by formula (4-1) and at least one compound selected from the group of compounds represented by formula (4-6).

18. The liquid crystal composition according to claim 14, wherein the fourth component is a mixture of at least one compound selected from the group of compounds represented by formula (4-1), at least one compound selected from the group of compounds represented by formula (4-4) and at least one compound selected from the group of compounds represented by formula (4-6).

19. The liquid crystal composition according to claim 13, wherein a ratio of the fourth component is from approximately 5% by weight to approximately to 60% by weight based on the total weight of the liquid crystal composition.

20. The liquid crystal composition according to claim 1, wherein the composition has a maximum temperature of a nematic phase of approximately 70° C. or more, an optical anisotropy (25° C.) at a wavelength of 589 nm of approximately 0.08 or more, and a dielectric anisotropy (25° C.) at a frequency of 1 kHz of approximately −2 or less.

21. The liquid crystal device display that includes the liquid crystal composition according to claim 1.

22. The liquid crystal composition according to claim 21, wherein the liquid crystal display device has an operation mode of a VA mode, an IPS mode or a PSA mode, and has a driving mode of an active matrix mode.

23. The compounds represented by formula (1-1):

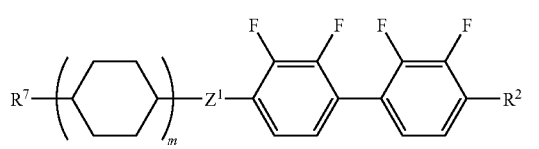

(1-1)

wherein $R^7$ is alkenyl having 2 to 12 carbons; $R^2$ is alkyl having 1 to 12 carbons, alkoxy having 1 to 12 carbons, alkenyl having 2 to 12 carbons or alkenyl having 2 to 12 carbons in which arbitrary hydrogen is replaced by fluorine; $Z^1$ is methyleneoxy or carbonyloxy; and m is 1 or 2.

* * * * *